United States Patent [19]

Allard et al.

[11] Patent Number: 4,838,863

[45] Date of Patent: Jun. 13, 1989

[54] SAFE NEEDLE SYSTEM FOR COLLECTING FLUIDS

[76] Inventors: Edward F. Allard, 7830 Greeley Blvd., Springfield, Va. 22152; Daniel Q. Longmire, 3410 Van Dyke St., Alexandria, Va. 22306

[21] Appl. No.: 99,013

[22] Filed: Sep. 21, 1987

[51] Int. Cl.[4] .............................................. A61M 5/00
[52] U.S. Cl. .................................... 604/110; 604/195; 604/198
[58] Field of Search ............... 604/110, 111, 195, 196, 604/198, 136, 197, 135, 137, 157

[56] References Cited

U.S. PATENT DOCUMENTS 3,306,290  2/1967  Weltman ............................. 604/197
4,542,749  9/1985  Caselgrandi et al. ............... 604/196
4,767,413  8/1988  Haber et al. ........................ 604/198

Primary Examiner—John D. Yasko

[57] ABSTRACT

A hypodermic syringe having a cylindrical outer body adapted to accept a smaller fluid storage vial within the inner walls thereof and having a removable cap on one end of said cylinder for providing access to insert and remove the vial with a spring loaded double headed needle assembly integrated into the other end thereof and held in place by a retainer until the storage has been punctured by one and of the needle, the vial filled and removed and the needle assembly retracted into the space vacated by the vial.

2 Claims, 2 Drawing Sheets

SAFE NEEDLE SYSTEM FOR COLLECTING FLUIDS

BACKGROUND OF THE INVENTION

1. Field of the Invention

This invention disclosure relates to the retraction of a needle into its syringe in such a way that the needle becomes inaccessible and is rendered non-operational when the needle is used to extract fluid from a body.

2. Description of the Prior Art

It is well known that diseases can be spread by re-using a needle from person to person. Also, a person can come in contact with a disease by being accidently cut by the needle. Hypodermic needles and syringes on the market today, used to extract blood and other fluids, have needles attached to a cylinder. After the needle has been used, it must be disposed of to prevent transmission of diseases.

But, before these needles are disposed they can expose people to disease because the needle can be re-used or an unsuspecting person can accidently cut himself/herself. Hospitals have machines that break off needles and destroy syringes but these machines are not available at a patient's bedside. In addition, needles carried on carts or placed on tables present a hazard to all workers in the vicinity of the needles.

There have been improvements in syringe technology, but there has been no technical improvements in needle safety outside of handling procedures.

SUMMARY OF THE INVENTION

The present invention effectively overcomes the problem of transmitting diseases by a needle.

The general purpose of this invention is to retract a needle into its holder after it has been used, rendering the needle inaccessible and non-reusable.

BRIEF DESCRIPTION OF DRAWINGS

FIG. 3 and FIG. 4 show that the spring and the needle head assembly cannot be put back into their original positions because the spring and needle are twisted from their original center line and would interfer with one another if the needle head assembly were pushed down.

DESCRIPTION OF THE PREFERRED EMBODIMENTS

Figure 4:
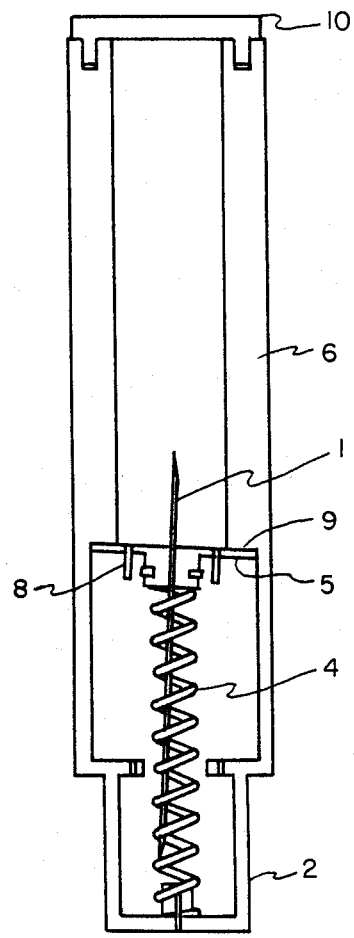
FIG. 3 and FIG. 4 show the needle in its retracted position.
Figure 1:
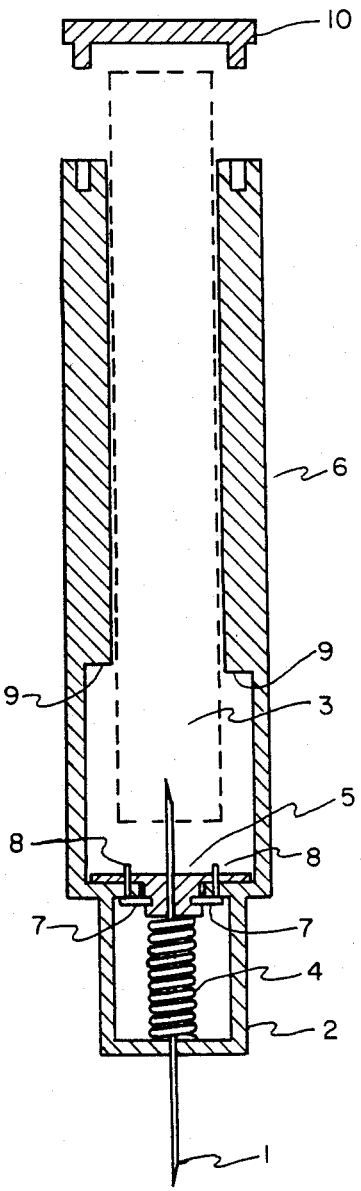
FIG. 1 shows a side view of a hypodermic needle used in this invention. The needle (1) is held in place by a spring holder (2). The bottom end of the needle is inserted into the body for the purpose of drawing fluid. The other end of a needle passes the fluid into a removable container (3) that begins filling when punctured by the needle. The spring (4) is under tension and tends to force the needle and needle head assembly (5) up into a container holder (6). Break-away tabs (7) hold the needle and needle head assembly which prevents the spring from retracting the needle. Tab breakers (8) are used to break the break-away tabs (7). When the container (3) is pushed down on the tab breakers (8), the breakers break the break-away tabs. After the break, the needle head is held down by the container. When the container is removed, the needle head assembly is driven up by the spring and stopped by the needle assembly stop (9). The cap (10) prevents liquid from leaking through the container holder.
Figure 3:
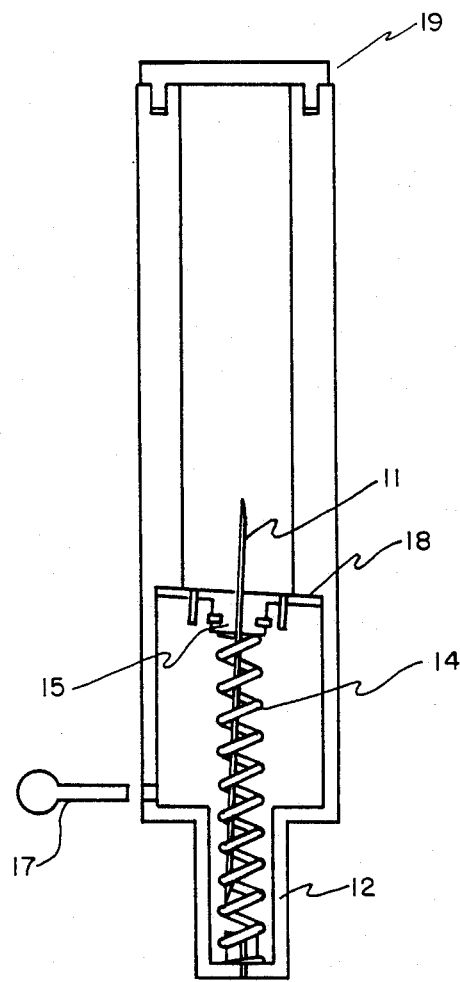

This invention perhaps may be best understood by making reference to the drawings. FIG. 1 shows a container holder with a spring loaded needle (1). The spring (4) tends to force the needle head assembly (5) up into the inside of the container holder (6). The spring is prevented from driving the head assembly into the container holder by break-away tabs (7). Tab breakers (8), when pushed down, sever or break the break-away tabs (7). When the break-away tabs are broken, the spring is free to push the needle head assembly (5) up into the container holder (6). The container (3) is used to push down on the tab breakers. When the break-away tabs are broken, the needle head assembly is free but held in place by the container (3). When the container (3) is removed, the head assembly is pushed into the container holder where it is prevented from continuing its movement by the needle assembly stop (9). The needle assembly stop (9) forces the needle off its center-line so that is becomes almost impossible to re-insert the needle through the spring holder. In addition, the absence of break-away tabs to hold down the spring makes it impossible for all practical purposes to reuse the needle. The needle is inaccessible and is rendered non-usable. Cap (10) prevents any residual fluid inside the container holder from leaking through the holder's opening at the top. The spring holder (2) prevents liquid from leaking through the hole left by the retracted needle by any of several known methods, not shown, such as a sealing membrane and sealing grommet at the protrusion point of needle 11 through the spring holder 12.

Figure 2:
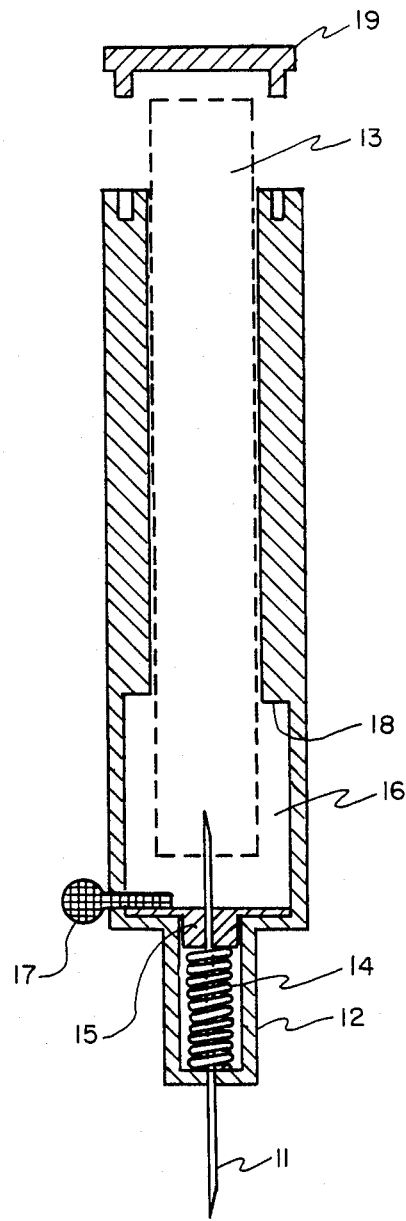
FIG. 2 shows a side view of a hypodermic needle used in this invention. The needle (11) is held in place by a spring holder (12). The bottom and end of the needle is inserted into a body for the purpose of drawing fluid. The other end of the needle passes the fluid into a removable container (13) that is punctured by the needle. The spring (14) is under tension and tends to force the needle head assembly (15) up into the container holder (16). The needle head assembly (15) is held in place by spring release (17). One or more removable containers (13) can be filled. When the nurse or operator of the needle is finished taking the fluid, the spring release (17) is pulled. This releases the needle head assembly (15) causing the spring to retract the needle (11). Needle stop (18) stops the head assembly. Cap (19) prevents fluid from leaking through the container holder.

FIG. 2 shows a container holder with a spring loaded needle (11). This container holder can be used more than once. It is a well established practice to press on the vein at the point of entry of the needle to stop the blood flow, whereupon the loaded container of blood can be removed and an empty container reinserted into the container holder when more than one container of blood is required. The container holder and needle are rendered non-usable when the spring release (17) is pulled. Needle (11) is spring loaded by spring (14). The needle assembly (15) is held in place by spring release (17). When the spring release (17) is pulled, the needle head assembly is driven into the container holder (16), where its upward movement is stopped by needle stop (18). This needle stop turns the needle away from its centerline, making the task of re-inserting the needle back into the spring holder practically impossible. Cap (19) prevents liquid from leaking through the container holder's opening at the top. The spring holder prevents liquid from leaking through the hole left by the retracted needle.

We claim:

1. A hypodermic needle wherein the needle is automatically retracted after use for rendering it inaccessible and non-usable, comprising a spring loaded needle open at each end, whereby fluid is drawn from one end and ejected through the other end whereby the ejected fluid is captured by a container and whereby the spring loaded needle is held in mechanical equilibrium by break-away tabs whereby the break-away tabs are broken by tab breakers whereby the force for the tab breakers is provided by pushing down on the container whereby when the tab holders are broken, the needle is free, whereby the freed needle is held in mechanical equilibrium until the container is removed whereby when the container is removed, the needle is pushed up into the container holder by the spring, whereby a stop prevents continued upward movement of the needle whereby the stop forces the needle from its centerline position whereby a cap prevents residual liquid inside the holder from leaking through its opening whereby a spring holder assembly holds the needle and spring in place and prevents liquid from leaking through the hole left by the retracted needle.

2. A hypodermic needle wherein the needle is retracted after use for rendering it inaccessible and non-reusable, comprising a spring loaded needle open at each end, whereby fluid is drawn from one end and ejected through the other end whereby the ejected fluid is captured by a container and whereby the spring loaded needle is held in mechanical equilibrium by a spring release, whereby when the spring release is pulled, the needle is forced by the spring into the container holder whereby its upward movement is stopped by a needle stop, whereby the needle stop forces the needle from its centerline position, whereby a cap prevents residual fluid inside the holder from leaking through its opening whereby a spring holder assembly holds the needle and spring in place and prevents liquid from leaking through the hole left by the retracted needle.

* * * * *